US012810418B2

(12) United States Patent
Sadeghi-Naini et al.

(10) Patent No.: US 12,810,418 B2
(45) Date of Patent: Nov. 24, 2026

(54) SYSTEMS AND METHODS FOR CHARACTERIZING INTRA-TUMOR REGIONS ON QUANTITATIVE ULTRASOUND PARAMETRIC IMAGES TO PREDICT CANCER RESPONSE TO CHEMOTHERAPY AT PRE-TREATMENT

(71) Applicants: SUNNYBROOK RESEARCH INSTITUTE, Toronto (CA); Ali Sadeghi-Naini, Maple (CA); Hamidreza Taleghamar, Toronto (CA)

(72) Inventors: Ali Sadeghi-Naini, Maple (CA); Hamidreza Taleghamar, Toronto (CA); Gregory J. Czarnota, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 206 days.

(21) Appl. No.: 18/573,142

(22) PCT Filed: Jun. 24, 2022

(86) PCT No.: PCT/CA2022/051020
§ 371 (c)(1),
(2) Date: Dec. 21, 2023

(87) PCT Pub. No.: WO2022/266774
PCT Pub. Date: Dec. 29, 2022

(65) Prior Publication Data

US 2024/0296559 A1 Sep. 5, 2024

Related U.S. Application Data

(60) Provisional application No. 63/215,353, filed on Jun. 25, 2021.

(51) Int. Cl.
*G06T 7/00* (2017.01)
*A61B 8/08* (2006.01)
*G06T 7/11* (2017.01)

(52) U.S. Cl.
CPC .......... *G06T 7/0012* (2013.01); *A61B 8/0825* (2013.01); *A61B 8/085* (2013.01);
(Continued)

(58) Field of Classification Search
CPC .................... G06T 7/0012; G06T 7/11; G06T 2207/10132; G06T 2207/20081;
(Continued)

(56) References Cited

U.S. PATENT DOCUMENTS

2018/0189947 A1 * 7/2018 Tadayyon .............. A61B 8/085
2022/0405932 A1 * 12/2022 Gaskill-Shipley ..... A61B 5/055

* cited by examiner

*Primary Examiner* — Stephen P Coleman
(74) *Attorney, Agent, or Firm* — Whiteford, Taylor & Preston LLP; Peter J. Davis

(57) ABSTRACT

A computer-implemented method for predicting tumor response to neoadjuvant chemotherapy, comprising: acquiring/generating, using an ultrasound device, ultrasound radiofrequency data and B-mode images from a tumor subject; identifying a region of interest, comprising a tumor, in each B-mode image; generating quantitative ultrasound (QUS) parametric map(s) by analysis of each RF frame associated with the B-mode images throughout the ROI to derive a corresponding QUS parameter; identifying distinct intra-tumor regions on the QUS parametric map(s) by applying a classification (clustering) algorithm to the QUS parametric map(s); extracting features from the intra-tumor regions on each of the QUS parametric map(s) to characterize the tumor; determining an optimal QUS biomarker for response prediction; training a classification algorithm for response prediction using the optimal QUS biomarker; and classifying the tumor subject into a responder or non-
(Continued)

responder to NAC using the optimal QUS biomarker with the trained classification algorithm.

25 Claims, 8 Drawing Sheets

(52) U.S. Cl.
CPC ...... *G06T 7/11* (2017.01); *G06T 2207/10132* (2013.01); *G06T 2207/20081* (2013.01); *G06T 2207/30068* (2013.01); *G06T 2207/30096* (2013.01)

(58) Field of Classification Search
CPC ........... G06T 2207/30068; G06T 2207/30096; A61B 8/0825; A61B 8/085; A61B 8/48; A61B 8/5207; A61B 8/5223; G16H 20/10; G16H 50/20; G16H 50/70; G16H 30/40; G06V 10/25
USPC .......................................................... 382/131
See application file for complete search history.

SYSTEMS AND METHODS FOR CHARACTERIZING INTRA-TUMOR REGIONS ON QUANTITATIVE ULTRASOUND PARAMETRIC IMAGES TO PREDICT CANCER RESPONSE TO CHEMOTHERAPY AT PRE-TREATMENT

FIELD

The following relates generally to systems and methods for predicting therapy response, and more particularly to systems and methods for characterizing intra-tumor regions on quantitative ultrasound parametric images to predict tumor response to anti-cancer therapies.

BACKGROUND

Quantitative ultrasound (QUS) techniques examine the frequency dependence of radiofrequency (RF) signals back-scattered from underlying tissue to extract parameters that quantify tissue physical properties, and can be used to characterize tissue micro-structure. Such QUS parameters include, but not limited to, mid-band fit (MBF), spectral slope (SS), spectral 0-MHz intercept (SI), effective scatterer diameter (ESD), and effective acoustic concentration (EAC), which can be used to derive parametric maps. No previous work has applied QUS parametric maps to quantify distinct intra-tumor regions for therapy response prediction.

SUMMARY

The inventors investigated the efficacy of QUS spectral multi-parametric imaging in characterizing LABC intra-tumor regions to predict tumor response to neoadjuvant chemotherapy (NAC) before the start of treatment. QUS spectral parametric images were generated using the ultrasound data acquired from 181 LABC patients at pre-treatment. The dataset was randomly partitioned into a training set (70%) and an independent test set (30%). A hidden Markov random field (HMRF) expectation maximization (EM) algorithm was applied to identify distinct intra-tumor regions on QUS multi-parametric images [43]. Several features were extracted from the segmented regions on different parametric maps within the tumor core and margin to characterize each tumor. The features were analyzed using a multi-step feature ranking and selection process to construct an optimal QUS biomarker consisting of four features for response prediction. For comparison, the features extracted from the unsegmented tumor core and margin were also analyzed and applied for predicting the therapy response. A decision tree model with adaptive boosting (AdaBoost) was adapted for classifying patients into responders and non-responders at pre-treatment. The patient responses to NAC identified after their surgery using standard clinical and pathological criteria were used as the ground truth to evaluate the performance of prediction models. Results indicated that the model with the developed biomarker could predict the NAC response of patients of the independent test set with a sensitivity and specificity of 87% and 85%, respectively. However, the models using barely features extracted from the unsegmented tumor core and the tumor margin predicted the NAC response with lower performance and an accuracy of up to 76.4%. Kaplan-Meier survival analyses showed that the patients predicted as responders using the optimal QUS biomarker demonstrated a statistically significantly better survival compared to those predicted as non-responders.

In an aspect of the presently disclosed subject-matter there is provided a computer-implemented method for predicting tumor response to neoadjuvant chemotherapy (NAC). The method comprises: acquiring, using an ultrasound device, ultrasound radiofrequency (RF) data, or ultrasound RF data and B-mode images, from a tumor subject prior to the NAC; generating, if not acquired at the acquiring step, the B-mode images using the acquired RF data; identifying a region of interest (ROI) in each of the B-mode images, the ROI comprising a tumor; generating at least one quantitative ultrasound (QUS) parametric map by QUS spectral analysis or analysis of envelop statistics of each RF frame associated with the B-mode images throughout the ROI to derive a corresponding QUS parameter, each of the at least one QUS parametric map based on a respective QUS parameter; identifying distinct intra-tumor regions on the at least one QUS parametric map by applying a classification (clustering) algorithm, such as K-means, Gaussian mixture models (GMMs), hidden Markov random field (HMRF) expectation maximization (EM) algorithm, or a clustering algorithm with spatial constraints followed by a consensus clustering algorithm, to the at least one QUS parametric map; extracting features from the intra-tumor regions on each of the at least one QUS parametric map within the ROI to characterize the tumor; determining an optimal QUS biomarker for response prediction; training a classification algorithm, such as decision tree with adaptive boosting, random forest, support vector machine (SVM), artificial neural networks, K nearest neighbours (K-NN), for response prediction using the optimal QUS biomarker; and classifying the tumor subject into a responder or a non-responder to the NAC using the optimal QUS biomarker in conjunction with the trained classification algorithm, the trained classification algorithm comprising a response prediction model.

BRIEF DESCRIPTION OF THE DRAWINGS

Various aspects will now be described by way of example only, with reference to the appended drawings in which.

Figure 4:
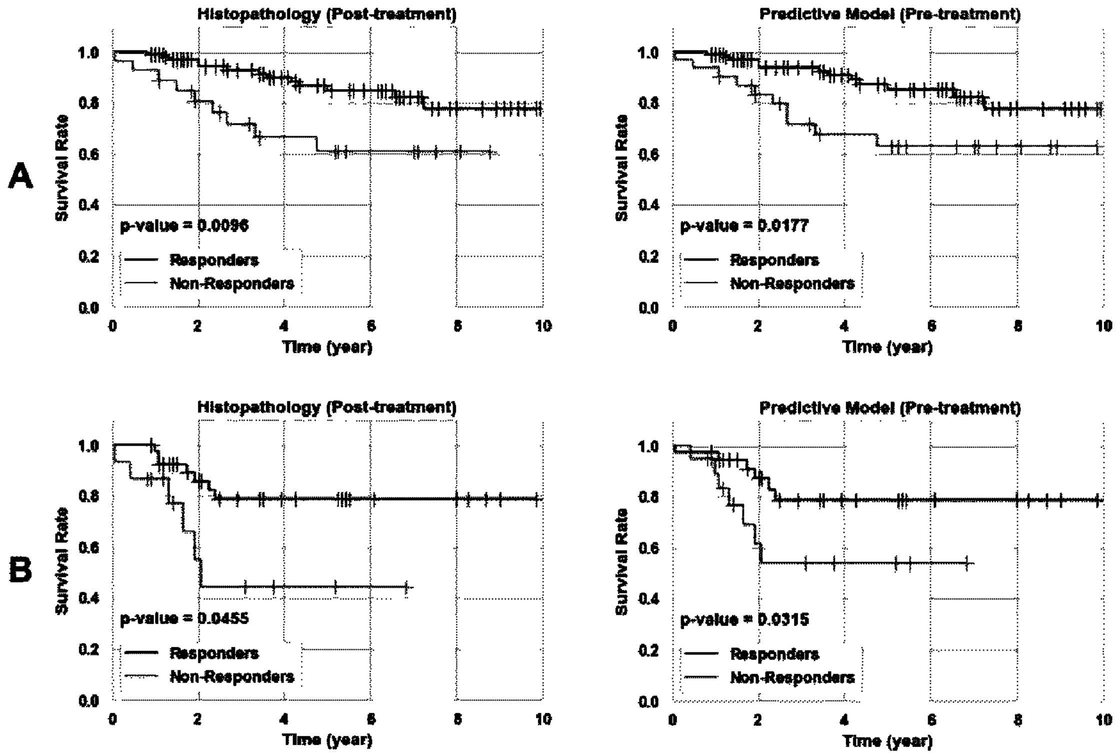
Figure 5:
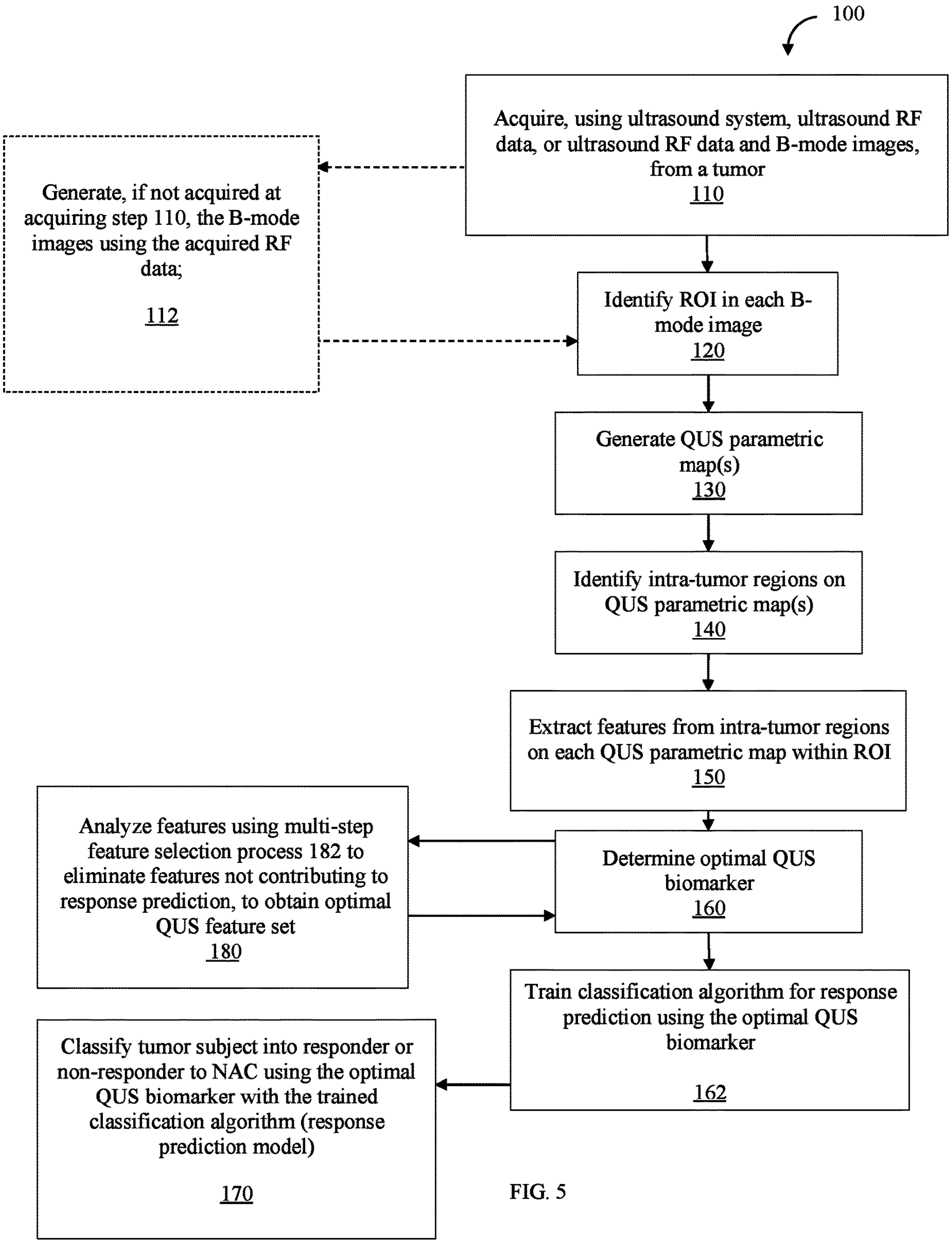
Figure 6:
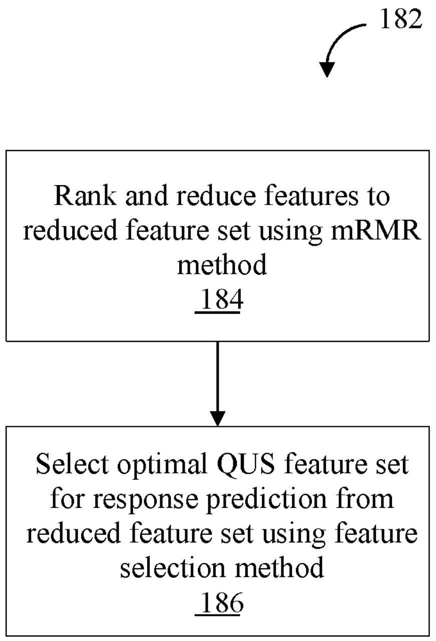
Figure 7:
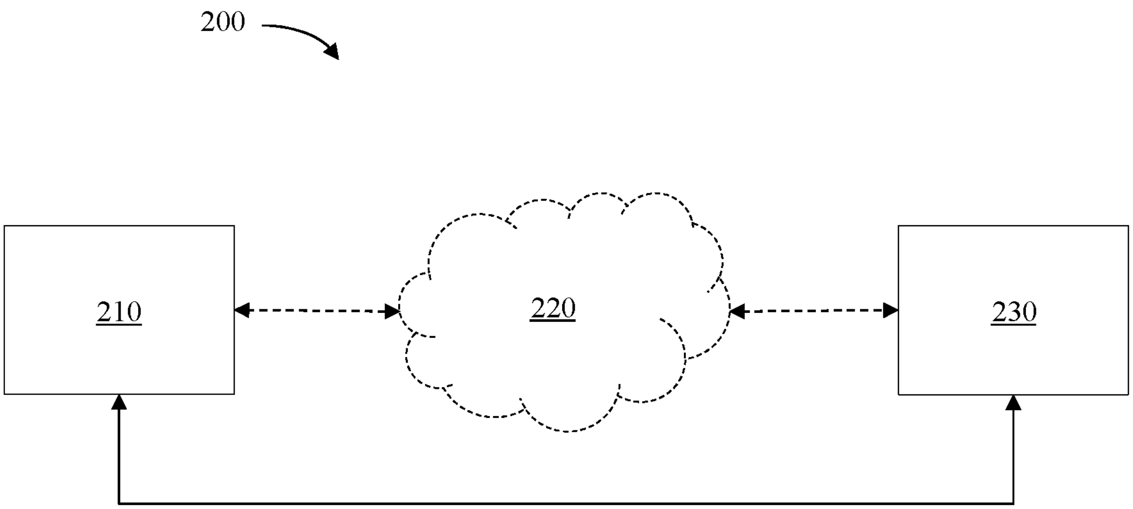
Figure 8:
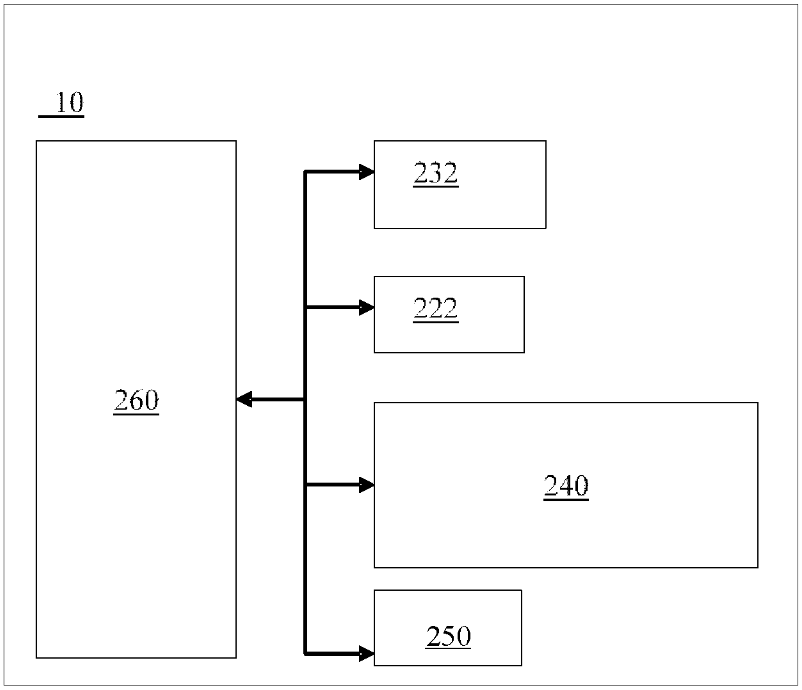
Figure 9:
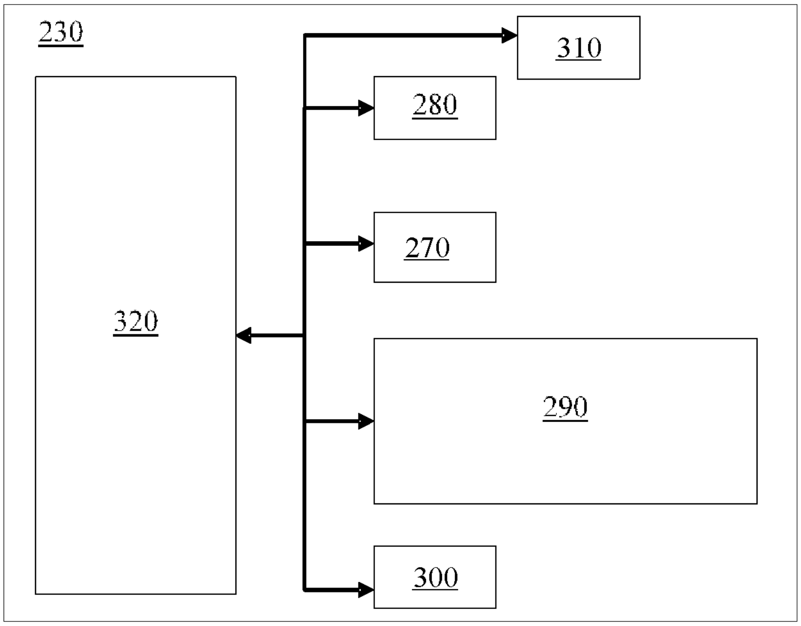

for the responders and non-responders in the training set;

FIG. 4 depicts ten-year recurrence-free survival curves for responding and non-responding patients in the training (A) and independent test set (B) identified at post treatment based on the clinical and histopathological criteria, and at pre-treatment using the developed predictive model with the optimal QUS biomarker;

FIG. 5 depicts a flow diagram of an example computer-implemented method in accordance with the presently described subject-matter;

FIG. 6 depicts a flow diagram of another example computer-implemented method in accordance with the presently described subject-matter;

FIG. 7 depicts a schematic diagram of an example system in accordance with the presently described subject-matter;

FIG. 8 depicts a schematic diagram of an example computing device in accordance with the presently described subject-matter; and FIG. 9 depicts a schematic diagram of an example ultrasound device in accordance with the presently described subject-matter.

DETAILED DESCRIPTION

Breast Cancer is the most frequent malignancy and the leading cause of cancer-related death among women [1], [2]. In 2018 more than 2 million new breast cancer cases were diagnosed, and more than 0.6 million people died from it [3]. Up to 20% of breast cancer patients are diagnosed with locally advanced breast cancer (LABC) that often presents as tumors greater than 5 cm in size, possibly with regional lymph node, skin and/or chest wall involvement [4], [5]. LABC patients have a high risk of relapse and metastasis. The standard treatments for LABC patients include a combination of neoadjuvant chemotherapy (NAC), followed by surgery, and if required, adjuvant radiation and/or hormonal therapies [4], [6]. Response to NAC has demonstrated a high correlation to the patient survival [6]-[8]. However, up to 40% of LABC patients do not respond to NAC, and complete pathological response is limited to only 10-30% of the patients [4], [5], [9]-[12]. Current methods for evaluating response to NAC are based on changes in tumor size in routine physical examination or anatomical imaging. However, changes in tumor size may require many weeks to months of therapy to be detectable, and in some cases, it is not evident despite a pathological response to NAC [13]. Post-surgical histopathology is the standard approach to determine tumor pathological response to NAC [7], [8], [14], [15]. However, at that point the window to adjust the NAC or switch to a salvage treatment is already closed. Prediction of LABC response to NAC before or early after the start of treatment can facilitate changing ineffective treatments to more effective ones. A personalized treatment strategy for LABC patients is expected to improve the rate of response to neoadjuvant therapies, and the overall survival and quality of life of the patients.

Genetic approaches have recently been investigated for prediction of cancer response to treatment [16]. Specifically, analysis of circulating tumor DNA has shown promise in evaluation of breast cancer response to therapy [17], [18]. Whereas such methods provide crucial scientific insights, they are invasive, relatively expensive, and require time-consuming analyses for quantification of circulating tumor DNA and gene sequencing. For monitoring and evaluating breast cancer response to NAC, functional imaging techniques including positron emission tomography (PET) and magnetic resonance imaging (MRI) have been investigated and shown promise within weeks after the treatment initiation [19]-[21]. However, these modalities are often expensive with long scan times and need injection of contrast agents to detect functional changes in tumor in response to treatment. Adapting an imaging modality with higher availability, lower cost, and an intrinsic source of image contrast to predict tumor response would facilitate adoption of the developed methodologies in routine clinical practice.

Ultrasound is a relatively inexpensive and portable imaging modality with a high spatial resolution and short imaging time that does not require injection of exogenous contrast agents. Quantitative ultrasound (QUS) techniques examine the frequency dependence of the radiofrequency (RF) signal backscattered from the underlying tissue to extract parameters that quantify tissue physical properties, and can be used to characterize tissue micro-structure [22]. Specifically, efficacy of the QUS parameters derived from the analysis of normalized power spectrum of RF signal or analysis of RF signal envelop statistics, including mid-band fit (MBF), spectral slope (SS), spectral 0-MHz intercept (SI), effective scatterer diameter (ESD), effective acoustic concentration (EAC), and homodyned K and Nakagami distribution parameters have been demonstrated in detecting and characterizing different abnormalities including prostate and breast cancer, intraocular tumors and cardiovascular disease [23]-[28].

A number of previous studies have demonstrated that changes in QUS spectral parameters after the start of treatment could be used to detect tumor cell death [29], and monitor breast cancer responses to chemotherapy [30]-[32]. Also, it has been demonstrated that compared to the QUS mean-value parameters, alterations in the textural characteristics of QUS spectral parametric maps have higher correlations to histological tumor cell death in response to chemotherapy [33], and could be used to predict LABC tumor response to NAC as early as one week after starting the treatment [34], [35]. Textural measures of the QUS parametric maps quantify the spatial relationship between local acoustic properties within the tumor and their early alterations after treatment initiation could characterize changes in response-related intra-tumor heterogeneity [35]. Sannachi et al. showed that a combination of QUS spectral and, textural parameters and molecular features of tumor could predict the LABC tumor response with high sensitivity and specificity [36]. In a recent study, Tadayyon et al. have demonstrated that a combination of QUS parameters derived from the tumor core and margin could be applied to characterize the responsiveness of LABC tumors to NAC before starting the treatment [37]. In particular, their study highlighted the importance of spatial heterogeneity within tumor core and margin in characterizing tumor aggressiveness and predicting its likelihood of response to standard chemotherapy at pre-treatment.

Imaging-based characterization of distinct intra-tumor regions has been shown efficacious for characterizing malignancies and predicting their therapy outcome [38], [39]. Intra-tumor regions evident on imaging can be linked to differential tumor biology and micro-structure, including clusters of heterogenous cancer cells, calcification foci, hypoxic or necrotic/apoptotic areas, and regions with different perfusion and metabolic activities [27], [35], [40],

[41]. A study by Byra et al. has demonstrated that features of intra-tumor regions identified using QUS maps of homodyned K distribution parameters could be used to differentiate benign and malignant breast lesions [39]. Another study by Wu et al. has showed the potential of characterizing intra-tumor regions on MRI in predicting pathological response of breast tumors to chemotherapy [42]. Despite its demonstrated potential for tissue characterization in various diagnostic and prognostic applications, no previous work has applied QUS parametric imaging to quantify distinct intra-tumor regions for therapy response prediction.

The inventors investigated for the first time the efficacy of quantitative ultrasound (QUS) multi-parametric imaging in conjunction with unsupervised classification algorithms in characterizing intra-tumor regions to predict breast tumor response to chemotherapy before the start of treatment. QUS multi-parametric images of breast tumors were generated using the ultrasound radiofrequency (RF) data acquired from 181 patients diagnosed with locally advanced breast cancer and planned for neo-adjuvant chemotherapy followed by surgery. A hidden Markov random field (HMRF) expectation maximization (EM) algorithm was applied to identify distinct intra-tumor regions on QUS multi-parametric images. Several features were extracted from the segmented intra-tumor regions and tumor margin on different parametric images. A multi-step feature selection procedure was applied to construct a QUS biomarker consisting of four features for response prediction. Evaluation results on an independent test set indicated that the developed biomarker coupled with a decision tree model with adaptive boosting (AdaBoost) as the classifier could predict the treatment response of patient at pre-treatment with an accuracy of 85.4% and an area under the receiver operating characteristic (ROC) curve (AUC) of 0.89. In comparison, the biomarkers consisted of the features derived from the entire tumor core (without consideration of the intra-tumor regions), and the entire tumor core and the tumor margin could predict the treatment response of patients with an accuracy of 74.5% and 76.4%, and an AUC of 0.79 and 0.76, respectively. Long-term survival analyses indicated that the patients predicted by the developed model as responders had a significantly better survival compared to the non-responders. Similar findings were observed for the two response cohorts identified at post-treatment based on standard clinical and pathological criteria. The results obtained by the inventors demonstrated the potential of QUS multi-parametric imaging integrated with unsupervised learning methods in identifying distinct intra-tumor regions in breast cancer to characterize its responsiveness to chemotherapy prior to the start of treatment.

With reference to FIG. 5, an example computer-implemented method 100 for predicting tumor response to neo-adjuvant chemotherapy (NAC) is provided. Method 100 may comprise: acquiring 110, using an ultrasound device, ultrasound radiofrequency (RF) data, or ultrasound RF data and B-mode images, from a tumor subject prior to the NAC; generating 112, if not acquired at said acquiring step 110, the B-mode images using the acquired RF data; identifying 120 a region of interest (ROI) in each of the B-mode images, the ROI comprising a tumor (which may comprise a tumor associated with any type of cancer, including but not limited to breast (including a locally advanced breast cancer or LABC), prostate, liver, or thyroid cancer); generating 130 at least one quantitative ultrasound (QUS) parametric map by QUS spectral analysis or analysis of envelop statistics of each RF frame associated with the B-mode images (i.e., associated with the image plane of each of the B-mode images) throughout the ROI to derive a corresponding QUS parameter, each QUS parametric map being based on a respective QUS parameter; identifying 140 distinct intra-tumor regions on the at least one QUS parametric map by applying a classification (clustering) algorithm, such as K-means, Gaussian mixture model (GMM), hidden Markov random field (HMRF) expectation maximization (EM) algorithm, or a clustering algorithm with spatial constraints followed by a consensus clustering algorithm, to the at least one QUS parametric map; extracting 150 features from the intra-tumor regions on each of the at least one QUS parametric map within the ROI to characterize the tumor (e.g., to characterize the intra-tumor regions and the tumor margin, such as in the QUS parametric maps of ESD, EAC, MBF, SI, SS, and homodyned K and Nakagami distribution parameters; determining 160 an optimal QUS biomarker for response prediction (e.g., by analyzing 180 the features using a multi-step feature selection process 182 to eliminate features that do not contribute to the response prediction, to obtain an optimal QUS feature set for the response prediction, the optimal QUS biomarker comprising the optimal QUS feature set); training 162 a classification algorithm for response prediction using the optimal QUS biomarker; and classifying 170 the tumor subject into a responder or a non-responder to the NAC using the optimal QUS biomarker in conjunction with the trained classification algorithm/response prediction model (such as a machine learning algorithm (e.g., a supervised, unsupervised, or reinforcement machine learning algorithm), including a decision tree model with adaptive boosting (AdaBoost), random forest, support vector machine (SVM), artificial neural network, or K nearest neighbours (K-NN) algorithm), the responder and non-responder classification determined, for example, by clinical and/or pathological ground truth classification criteria including, but not necessarily limited to, pathological complete response (pCR) versus non-pCR, or a modified response (MR) grading system based on response evaluation criteria in solid tumors (RECIST) and histopathological criteria, with a MR indicating less than 30% reduction in tumor size comprising a non-responder, and a MR indicating 30% or greater reduction in tumor size or low residual tumor cellularity comprising a responder.

With reference to FIG. 6, the multi-step feature selection process 182 may comprise, for example: ranking and reducing 184 the features to a reduced feature set using a minimal-redundancy-maximal-relevance (mRMR) method; and selecting 186 the optimal QUS feature set for the response prediction from the reduced feature set using a feature selection method comprising, e.g., sequential forward selection (SFS), sequential backward selection, or least absolute shrinkage and selection operator (LASSO).

Described below is an example application of the presently described subject-matter, wherein methods 100, 182 are applied to predict tumor response to neoadjuvant chemotherapy (NAC).

1. Materials and Methods

1.1. Study Protocol

The inventors' study was conducted in accordance with institutional research ethics board approval from Sunnybrook Health Sciences Centre™ (SHSC), Toronto, Canada. The study was open to all women who were diagnosed with LABC aged 18-85 and planned for NAC followed by surgery. In accord with this, 181 eligible patients were recruited for the study after obtaining written informed consent. A core needle biopsy was performed for all patients to confirm cancer diagnosis, and determine the tumor grade and histological subtype. Also, for each patient pre-treatment magnetic resonance (MR) images of the breast were acquired to determine the initial tumor size. Ultrasound data were acquired from the patients immediately before the start of NAC. Ultrasound scans were performed with patients lying supine with their arms above their heads. Patients were followed up to 10 years after their treatment and their clinical data were recorded for recurrence-free survival analysis. For the study, about 30% of patients (n=53) were randomly selected and separated to form an unseen independent test set, and the remaining patients (n=128) were considered as the training set.

1.2. Clinical and Pathological Response Evaluation

All patients had breast surgery after completing their neoadjuvant chemotherapy for assessing residual tumor size, an MRI scan of the breast was obtained right before the surgery. The surgical specimens were stained with hematoxylin and eosin (H&E) and prepared when possible on whole-mount 5"× 7" pathology slides which were digitized using a confocal scanner (TISSUEscope™, Huron Technologies™, Waterloo, Ontario, Canada). All pathology samples were examined by a board-certified pathologist who remained blinded to the study results. Patients were categorized into two groups of responders and non-responders using a modified response (MR) grading system which was based on response evaluation criteria in solid tumors (RECIST) [44] and histopathological criteria [37][45]. The MR score was defined as follows: MR 1: no reduction in tumor size; MR 2: up to 30% reduction in tumor size; MR 3: 30% to 90% reduction in tumor size or a very low residual tumor cellularity determined histopathologically; MR 4: more than 90% reduction in tumor; MR 5: no evident tumor and no malignant cells identifiable in sections from the site of the tumor; only vascular fibroelastotic stroma remaining, often containing macrophages; nevertheless, ductal carcinoma in situ may be present. The patients with a MR score of 1-2 (less than 30% reduction in tumor size) and 3-5 (30% or greater reduction in tumor size or with very low residual tumor cellularity) were determined as non-responders and responders, respectively. In accordance with this, 138 and 43 patients were determined as responders and non-responders, respectively.

1.3. Ultrasound Data Acquisition

Ultrasound data were obtained using an RF-enabled Sonix RP™, (Ultrasonix™, Vancouver, Canada) system utilizing an L14-5/60 transducer, operating at the center frequency of ~6 MHz, and with a −6 dB bandwidth range of 3-8 MHz. For each breast tumor, ultrasound RF data and B-mode images were acquired at four to seven image planes across the breast with approximately 1 cm intervals. An expert clinician selected the breast region for ultrasound scanning and determined acquisition scan planes via a physical examination of the patient. The image size along the lateral and axial directions was 6 cm and 4-6 cm, respectively. The focal depth was set at the center of the tumor depending on the individual patient circumstances. The RF data was acquired with a sampling frequency of 40 MHz and digitized with 16-bit resolution.

1.4. Parametric Map Generation

For generating the QUS parametric images, the tumor core was manually outlined by experts on each scan plane using the associated B-mode image, although such manual operation may instead be achieved digitally, and automatically, by artificial intelligence and/or machine learning algorithms employed on an appropriate digital image processing system. In addition, the tumor margin contour was automatically generated with a thickness of 5 mm around the core (although different margin dimensions are possible, such as a margin from approximately 1 mm to approximately 10 mm wide, or approximately 5% to approximately 200% of the tumour core diameter). The parametric maps were generated for all imaging planes of the tumor using a sliding window analysis throughout the entire region of interest (tumor core and margin) with windows of size 2 mm×2 mm and 95% overlap in both lateral and axial direction.

The QUS spectral analyses were performed to derive MBF, SS, SI, ESD, EAC parameters [26], [27]. The power spectrum was calculated using the Fourier transform of the Hanning-gated RF data for every scan line within the analysis window and then averaged. A reference phantom technique was used to normalize the average power spectrum to remove the effects of the system transfer function and transducer beam-forming [46], [47]. The reference phantom was composed of 5 to 30 μm diameter glass beads embedded in a homogeneous background of microscopic oil droplets in gelatin (Medical Physics Department, University of Wisconsin, USA). The attenuation coefficient and speed of sound parameters of the reference phantom were 0.576 dB/MHz·cm and 1488 m/s, respectively. The attenuation coefficient estimate (ACE) of tumor was calculated using a spectral difference method [46], and used for attenuation correction of the normalized power spectrum using the point attenuation compensation method. A two-layer (intervening tissue and tumor) attenuation correction was performed using total attenuation estimation [46]. An attenuation coefficient of 1 dB/MHz·cm was assumed for intervening breast tissue based on ultrasound tomography measurements of the breast [48]. The MBF, SS and SI parameters were estimated using a linear regression analysis within the −6 dB bandwidth of the transducer [26], [49], [50]. The ESD and EAC parameters were derived by fitting a spherical Gaussian form factor model to the estimated backscatter coefficient [51], [52].

1.5. Segmentation of Intra-Tumor Regions

The intra-tumor regions were identified at pixel level on QUS parametric images using a HMRF-EM algorithm and the tumor core parametric maps of ESD, EAC, MBF and SI as different data channels (described further below). The optimum number of distinct regions within tumors was determined using the Elbow method over the samples of the training set [53]. Specifically, the intra-tumor segmentation was performed for different number of regions, and the Bayesian information criterion (BIC) was estimated as the clustering quality metric (although the clustering quality metric may comprise BIC, Calinski-Harabasz index, or Davies-Bouldin index). Subsequently, the least number of regions associated with an appropriate clustering quality metric (in this example, a low BIC (the elbow point in the plot of BIC versus different number of regions)) was identified. Using this method, the optimum number of distinct intra-tumor regions on the QUS parametric maps was determined as three regions.

A modified HMRF model was trained using an EM algorithm for segmentation of intra-tumor regions [43]. The HMRF-EM is an unsupervised classification method originally proposed for computer vision applications [54]. This method can be adapted for segmentation of multi-channel color images [43], and medical imaging data [43], [55]. In this work, the inventors applied different QUS parametric maps as different channels of data (features) to segment intra-tumor distinct regions. For each pixel i (i=1, . . . , N), the feature set can be defined as $$x_i = \{I_i^{ESD}, I_i^{EAC}, I_i^{MBF}, I_i^{SI}\}.$$

The goal is to infer the labels $Y=(y_1, y_2, \ldots, y_N)$ where $y_i=\{1,2,3\}$, for all tumor core pixels within a set of parametric maps $X=(x_1, x_2, \ldots, x_N)$ with maximum a posteriori probability (MAP) estimation. In other words, the estimated labels Y* should satisfy:

$$Y^* = \text{argmax}_y\{P(X|Y, \theta)P(Y)\} \quad (1)$$

Where the prior probability P(Y) is a Gibbs distribution and θ is representative of multivariate Gaussian distribution parameters. The following equation is used for the joint likelihood probability:

$$P(X|Y, \theta) = \prod_i P(x_i|Y, \theta) = \prod_i P(x_i|y_i, \theta_i) \quad (2)$$

Where $P(x_i|y_i, \theta_i)$ is a multivariate Gaussian distribution with parameters $\theta_{x_i}=(\mu_i, \Sigma_i)$, such that $\mu_i$ is the mean and $\Sigma_i$ is the precision matrix of the distribution. The modified HMRF-EM algorithm was used to solve Equation (1). To estimate initial parameters and labels, a K-means algorithm was applied on the parametric maps. Then, the following steps were performed iteratively:

1. Compute the likelihood distribution $P^t(x_i|y_i, \theta_i)$ in step t.
2. Use the current parameter set et to estimate the labels by the MAP estimation algorithm [43].
3. Calculate the posterior distribution $P^t(l|x_i)$ for all the $l \in \{1,2,3\}$ and all pixels x; utilizing the Bayesian rule.
4. Compute the updated parameter set $\theta^{t+1}$ with calculated posterior distribution.

The inventors performed the iteration on the whole training set for 15 times or until convergence, and repeated the inner loop in the MAP estimation algorithm for 10 times or until convergence. Subsequently, the estimated Gaussian distribution parameters (θ) were used with the MAP estimation algorithm to determine the labels of the pixels in the parametric maps of the test set. The segmented regions were numbered based on the mean-value in the MBF parametric maps of the training set from the highest (first region) to the lowest (third region) values.

1.6. Feature Extraction and Biomarker Discovery

A total of 56 features were extracted from the segmented intra-tumor regions and the tumor margin in the QUS parametric maps of ESD, EAC, MBF and SI. The extracted features included mean-value and signal to noise ratio (SNR) (and may also include statistical and textural features) of each parametric map within the tumor core (4×2 features), mean-value and SNR (and may also include statistical and textural features) of each parametric map within the tumor margin (4×2 features), mean-value and SNR (and may also include statistical and textural features) of each parametric map within each segmented region (4×3×2 features), the difference between the mean-value (and may also include statistical and textural features) of each two segmented regions in each parametric map (4×3 features), the proportion area of each segmented region within the tumor core (3 features), and the relative area of the tumor margin to the core. The SNR of each region was acquired by calculating the ratio of the average pixel value to the standard deviation of pixel values of the region, as a measure of spatial heterogeneity [56]. The features were calculated for all 2D imaging planes associated with each tumor and subsequently averaged over the entire tumor volume.

A multi-step feature reduction/selection process was applied to eliminate the redundant and irrelevant features that do not contribute to the predictive model and obtain an optimal QUS feature set for robust response prediction. In the first step, the features were ranked and reduced to 21 features using the minimal-redundancy-maximal-relevance (mRMR) method [55]. In the next step, the final features were selected from the reduced feature set using a sequential forward selection (SFS) method. A 5-fold cross-validated accuracy on the training set was used as the criterion in the SFS method with an AdaBoost decision tree model as the classifier [59]. The SFS method selected four features as the optimal QUS feature set (biomarker) that was applied for training the response prediction model. It will be appreciated that the number of extracted features may be other than 56, the number of features in the reduced feature set may be other than 21, and the number of optimal features may be other than four, depending on whether the extracted features comprise other than those described above (e.g., if they also include, e.g., statistical and textural features), the method(s)/parameter(s) used to select the reduced feature set and optimal features (e.g., if methods other than mRMR and SFS (such as sequential backward selection or least absolute shrinkage and selection operator (LASSO)) are used), and possibly, the training data applied.

Two other experiments were conducted for comparison using the features extracted from the entire tumor core without considering any intra-tumor regions, and the tumor margin. Specifically, eight features including the mean-value and SNR of each parametric map within the tumor core (4×2 features), and 16 features consisted of the mean-value and SNR of each parametric map within the tumor core (4×2 features) and the tumor margin (4×2 features) were applied in these experiments, respectively. In both cases, the best feature set was selected using a similar SFS method as described above. The best feature sets included four features in both experiments, and were separately applied for response prediction as described below.

1.7. Response Prediction and Risk Assessment

To address the imbalance issue of the dataset, the minority class in the training set was oversampled to the size of the majority class using the synthetic minority oversampling technique (SMOTE) [57]. An AdaBoost decision tree model was adapted for response prediction in each experiment. After training each model on the oversampled training set, its performance was evaluated on the independent test set using the accuracy, sensitivity, specificity, and the area under the receiver operating characteristic (ROC) curve (AUC).

Survival analysis was performed to assess the efficacy of the developed QUS biomarker at pre-treatment in differentiating the LABC patient cohorts with different recurrence-free survival determined many years later. The Kaplan- Meier survival curves were generated for the responders and non-responders identified based on the model's prediction at pre-treatment, and at post-treatment based on the clinical and histopathological criteria. A log-rank test was used to assess for statistically significant differences between the survival curves of the two patient cohorts (responders versus non-responders).

2. Results

The clinical and histopathological characteristics of the participating patients are provided in Table 1:

TABLE 1

Patient characteristics

| Characteristic | Mean ± SD/Percentage |
|---|---|
| Age | 50.6 ± 11.5 years |
| Initial Tumor Size | 5.2 ± 2.7 cm |
| Residual Tumor size | 2.5 ± 3.4 cm |
| **Histology** | |
| Invasive Ductal Carcinoma | 90.3% |
| Invasive Lobular Carcinoma | 3.4% |
| Invasive Metaplastic Carcinoma | 6.3% |
| **Tumor Grade** | |
| Grade I | 10.6% |
| Grade II | 38.8% |
| Grade III | 50.6% |
| **Molecular Features** | |
| ER+ | 63.4% |
| PR+ | 54.7% |
| HER2+ | 34.3% |
| Triple Negative | 24.4% |
| ER+/PR+/HER2+ | 18.6% |
| ER+/PR+/HER2− | 33.7% |
| ER−/PR−/HER2+ | 10.5% |
| **Response** | |
| Responders | 76.2% |
| Non-Responders | 23.8% |

The average age of the patients was 50.6 years. The patients had an average initial tumor size of 5.2 cm, and at the end of their treatment, the average residual tumor size was 2.5 cm. In terms of histology, 90.3% of the tumors were diagnosed with invasive ductal carcinoma, 3.4% with invasive lobular carcinoma, and 6.3% with invasive metaplastic carcinoma. Further, 10.6% of the patients were diagnosed with grade 1 tumors, 38.8% with grade 2 tumors, and 50.6% with grade 3 tumors. At the end of the treatment, 76.2% of the patients were identified as responders, and 23.8% as non-responder, according to the clinical and histopathological criteria.

Figure 1:
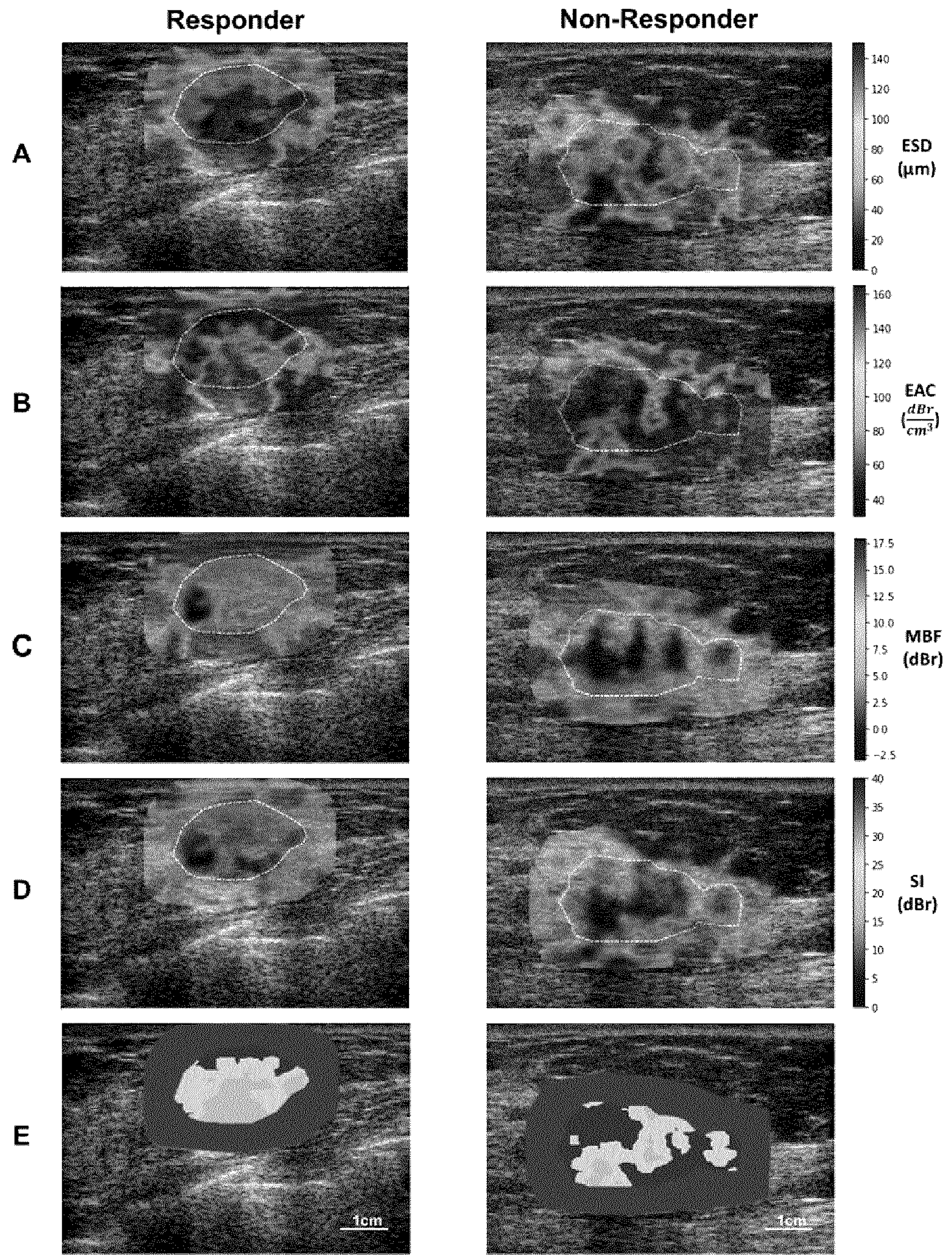
FIG. 1A depicts ultrasound B-mode images with parametric overlays of ESD acquired from a representative responder and non-responder to NAC, with the tumor core outlined with white dashed line.
FIG. 1B depicts ultrasound B-mode images with parametric overlays of EAC acquired from a representative responder and non-responder to NAC, with the tumor core outlined with white dashed line.
FIG. 1C depicts ultrasound B-mode images with parametric overlays of MBF acquired from a representative responder and non-responder to NAC, with the tumor core outlined with white dashed line.
FIG. 1D depicts ultrasound B-mode images with parametric overlays of SI acquired from a representative responder and non-responder to NAC, with the tumor core outlined with white dashed line.
FIG. 1E depicts distinct intra-tumor regions segmented using the HMRF-EM algorithm, surrounded by the tumor margin area.
Figure 2:
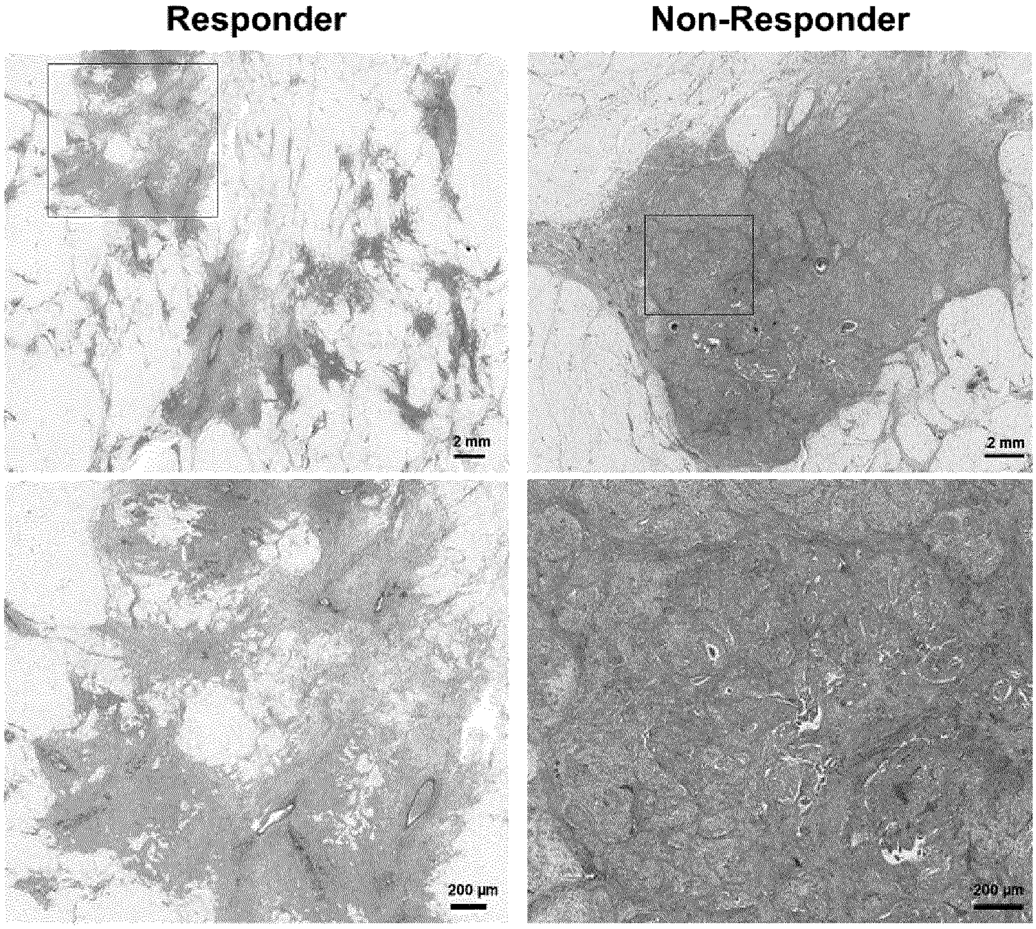
FIG. 2 depicts whole mount histopathology images of mastectomy specimens acquired from representative responding and non-responding patients, at low (top) and high (bottom) magnifications, the scale bars representing 2 mm and 200 μm in low and high-magnification images, respectively.

FIG. 1 demonstrates QUS parametric maps of ESD, EAC, MBF and SI overlaid on ultrasound B-mode images acquired from representative responding and non-responding patients, respectively. Distinct intra-tumor regions identified using the HMRF-EM algorithm are presented in FIG. 1-E. The QUS parametric maps obtained from the responding and non-responding patients were different in terms of mean and spatial distribution of pixel values. A considerable difference was observed in size, and the mean, distribution and difference of the pixel values of the intra-tumor segmented regions on the QUS parametric maps acquired from the responders and non-responders. FIG. 2 shows H&E stained histopathology images of the surgical specimens obtained from representative responding and non-responding patients. Whereas the histology images show a large residual tumor in the mastectomy specimen of the non-responding patient, the images acquired from the responding patient demonstrate the tumor bed area with chemotherapy effects and no residual tumor. The images also show considerable heterogeneity within the tumor (bed) area.

The multi-step feature selection process resulted in a QUS biomarker for NAC response prediction with four features out of 56 features including mean-value of the MBF parametric map within the first segmented region $$(M_1^{MBF}),$$

SNR of the ESD parametric map within the tumor margin $$(SNR_m^{ESD}),$$

SNR of the SI parametric map within the first region $$(SNR_1^{SI}),$$

and the difference between mean-values of the EAC parametric map within the first and third regions $$(M_{3-1}^{EAC}).$$

Figure 3:
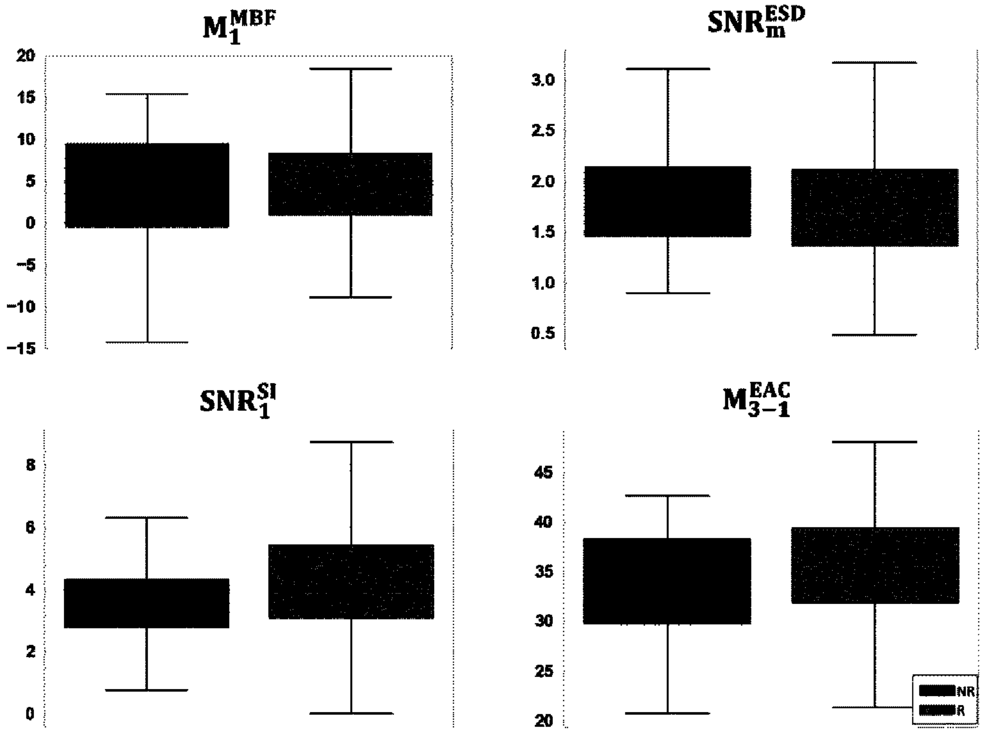
FIG. 3 depicts box plots of features including $$M_1^{MBF}, SNR_m^{ESD}, SNR_1^{SI} \text{ and } M_{3-1}^{EAC}$$

The first and third regions are associated with the highest and lowest mean-values in the MBF parametric maps. FIG. 3 demonstrates the box plots of the selected features for responders and non-responders in the training set. Whereas various levels of difference can be observed in the selected features between the responders and non-responders, a combination of these features is expected to differentiate better between the response groups at pre-treatment.

Applying a similar feature selection method on the eight features derived from the unsegmented tumor core resulted in four features including mean-value of the MBF and SI parametric maps $$(M_C^{MBF} \text{ and } M_C^{SI}),$$

and SNR of the EAC and SI parametric map $$(SNR_C^{EAC} \text{ and } SNR_C^{SI})$$

within the tumor core. In case of the 16 features derived from the unsegmented tumor core and the tumor margin the best feature set consisted of mean-value of the MBF and SI parametric maps within the tumor core $$(M_C^{MBF} \text{ and } M_S^{SI}),$$

SNR of the EAC parametric map within the tumor core $$(SNR_C^{EAC})$$

and SNR of the SI parametric map within the tumor margin $$(SNR_m^{SI}).$$

Table 2 presents the result of response prediction on the training and independent test sets using the best feature sets obtained in different experiments:

TABLE 2

Results of response prediction on the training and independent test sets using different QUS feature sets. Acc: Accuracy; Sen: Sensitivity; Spec: Specificity.

| | Training Set | | | | Test Set | | | |
|---|---|---|---|---|---|---|---|---|
| Feature Set | Acc | Sen | Spec | AUC | Acc | Sen | Spec | AUC |
| Unsegmented Core: $M_C^{MBF}$, $M_C^{SI}$, $SNR_C^{EAC}$, $SNR_C^{SI}$ | 81.0% | 81.5% | 80.8% | 0.853 | 74.5% | 66.6% | 77.5% | 0.79 |
| Unsegmented Core and Margin: $M_C^{MBF}$, $M_C^{SI}$, $SNR_C^{EAC}$, $SNR_m^{SI}$ | 81.0% | 77.8% | 81.8% | 0.86 | 76.4% | 66.6% | 80.0% | 0.76 |
| Intra-Tumor Regions and Margin: $M_1^{MBF}$, $SNR_m^{ESD}$, $SNR_1^{SI}$, $M_{3-1}^{EAC}$ | 90.5% | 88.9% | 91.0% | 0.974 | 85.4% | 86.6% | 85.0% | 0.89 |

Applying the selected features among those extracted from the unsegmented tumor core in response prediction resulted in an accuracy of 74.5%, a sensitivity of 66.6%, and a specificity of 77.5% on the independent test set. Incorporating the features derived from the tumor margin increased the specificity to 80% and the accuracy to 76.4%. Applying the QUS biomarker consisting of the features derived from the segmented intra-tumor regions and the tumor margin resulted in the best performance of the response prediction model on both the training and test sets, with an accuracy, sensitivity, specificity, and AUC of 85.4%, 86.6%, 85.4%, and 0.89, respectively, on the independent test set.

FIG. 4 demonstrates the ten-year recurrence-free survival curves for the responding and non-responding patients identified based on prediction at pre-treatment using the optimal QUS biomarker, and at post-treatment using the clinical and pathological criteria. Statistically significant differences ($p\text{-value}<0.05$) were observed between the survival curves of the histopathological response cohorts in both the training and test sets, and responders demonstrated a significantly higher survival rate compared to non-responders. Similar trends were observed in the survival curves of the response cohorts predicted at pre-treatment, with statistically significant differences between the long-term survival of the two cohorts in both the training and test sets.

3. Discussion

The inventors investigated a novel method to predict breast cancer response to NAC using the characteristics of distinct intra-tumor regions on QUS multi-parametric images acquired at pre-treatment. A modified HMRF-EM algorithm was applied to segment the intra-tumor regions on QUS parametric images acquired from LABC patients. Several features were derived from the segmented QUS multi-parametric images to characterize the identified intra-tumor regions and tumor margin. A hybrid QUS biomarker consisting of four features was constructed through a multi-step feature selection process for NAC response prediction. Results indicated that the developed QUS biomarker in conjunction with an AdaBoost decision tree model could predict the response of LABC patient to NAC before starting the treatment with an accuracy of 85.4% and an AUC of 0.89. In comparison, applying the best features extracted from the whole tumor core and the tumor margin on the QUS parametric images resulted in an accuracy of 76.4% and an AUC of 0.76. The obtained results show that using characteristics of distinct intra-tumor regions identified on the QUS multi-parametric images can improve the accuracy of therapy response prediction in breast cancer. Recurrence-free survival analyses were performed to evaluate the performance of the developed predictive model in differentiating patients in terms of long-term treatment outcomes. The ten-year recurrence-free survival curves obtained for the responders and non-responders identified based on prediction at pre-treatment were very similar to their counterparts generated for the two response groups identified at post-treatment using the clinical and histopathological criteria. Statistically significant differences were observed between the survival of the responders and non-responders identified based on the both methods.

A number of recent studies has demonstrated the potential of QUS spectral and textural parameters to predict and monitor response of breast cancer to chemotherapy [34]-[37]. Those studies evaluated the efficacy of QUS parameters for therapy response evaluation using a leave-one-patient-out cross-validation approach due to the relatively small size of their dataset. Whereas cross-validation approaches are commonly used in evaluating classification models when limited data are available, they may overestimate a model's performance due to overfitting. The inventors introduced a new method for analyzing the QUS multi-parametric images for response prediction by quantifying the properties of intra-tumor regions. The developed QUS biomarker was evaluated on an independent test set that was kept unseen during the biomarker discovery and predictive model training. The results obtained by the inventors show the efficacy of QUS parameters for therapy response evaluation based on new robust features that were assessed rigorously on independent data.

The results indicated that characteristics of intra-tumor regions and tumor margin identified on QUS parametric maps of ESD, EAC, MBF, and SI could be used for predicting tumor response (including that of a breast tumor, including LABC) to chemotherapy prior to start of treatment. These parametric maps provide complementary information regarding the tumor microstructure by quantifying the properties of underlying acoustic scatterers including their size, density, distribution and impedance mismatch

[22], [23], [26]. Segmenting the distinct regions on these multi-parametric maps potentially facilitates effective characterization of intra-tumor heterogeneity. Spatial heterogeneity within tumor has demonstrated a crucial role in its responsiveness/resistance to anti-cancer therapies and clinical outcome [38].

The optimal QUS biomarker developed through a multi-step feature selection process consists of four features including $$M_1^{MBF},\ SNR_m^{ESD},\ SNR_1^{SI},\ \text{and}\ M_{3-1}^{EAC}.$$

The selected features imply that the four QUS parametric maps provide complementary information about the responsiveness of tumors, including breast tumors, to chemotherapy, as all the four parametric images have contributed to the developed biomarker. Further, the features derived from the distinct intra-tumor regions may better characterize a tumor in terms of therapy response as the feature selection algorithm prioritizes those over the features derived from the entire tumor core. The second feature in the biomarker $$(SNR_m^{ESD})$$

is a measure of signal quality (homogeneity) in effective scatterer dimeters within the tumor margin.

In conclusion, the inventors demonstrated that intra-tumor regions in tumors, including breast tumors (e.g., LABC), could effectively be segmented on QUS multi-parametric maps for chemotherapy response prediction. The QUS biomarker developed using this methodology could predict the tumor (including breast tumor) response to NAC with high sensitivity and specificity and classify patients into two cohorts with significantly different long-term outcomes. Predicting cancer response to chemotherapy at pre-treatment with demonstrated correlations to long-term survival may facilitate adoption of precision medicine for cancer patients.

With reference to FIG. 7, any of the methods described herein may be executed by a system 200 comprising one or more computing device(s) 210 (which may comprise server(s) 210) specially designed and configured with appropriate processing capability (including with respect to general and special purpose (such as graphics) processing in order to execute steps of the methods 100, 182 described herein, including the machine learning and data acquisition and processing steps, including image processing and generating steps (such as the QUS spectral analysis and QUS multi-parametric map(s) or image(s) generation steps)). The system 200 may further comprise one or more ultrasound device(s) 230 for acquiring and/or generating ultrasound radiofrequency (RF) data and B-mode or 2D images of tissue. Computing devices 210 and ultrasound devices 230 may communicate directly, or indirectly, over network 220, via any of the network types and communication protocols described herein.

Network 220 may comprise a direct link between communicating components of system 200, or an indirect one, including but not limited to communication by Ethernet™, Bluetooth™, WiFi™, NFC (near-field communication), infrared, WiMAX™ (fixed or mobile), RFID (radio-frequency identification), CoAP (Constrained Application Protocol), MQTT (Message Queue Telemetry Transport), and any suitable cellular communications protocols including, but not limited to, up to 5G protocols, such as GSM, GPRS, EDGE, CDMA, UMTS, LTE, LTE-A, IMS, for example, and any other wired or wireless communications protocols and mediums suitable for the method(s), system(s) and device(s) described herein, including any proprietary protocols. Network 220 may comprise a single network or more than one interconnected network, of any type suitable for the method(s), system(s) and device(s) described herein, including but not limited to wired or wireless PANs (personal area networks), LANs (local area networks), WANs (wide area networks), MANs (metropolitan area networks), mesh or ad hoc networks, VPNs (virtual private networks), the Internet, and any other suitable network type, in any suitable network configuration or topology (e.g., mesh, token ring, tree, star, etc.). Although not shown in FIG. 7, system 200 may further include any components necessary to effect the communication and/or network type(s) used, and may also include components for increased network security, for example, access points, routers, and firewalls.

Referring to FIG. 8, computing device 210 may comprise memory 222, communication module 232, a display 240, one or more input devices 250, and at least one processor 260 coupled to the memory 222, communication module 232, display 240, and input device(s) 250. Communication module 232 enables computing device 210 to communicate with one or more other components of system 200, such as one or more ultrasound devices 230, via a wired or wireless communication network, such as network 220.

With reference to FIG. 9, ultrasound device 230 may comprise memory 270, communication module 280, a display 290, one or more input devices 300 (including a keyboard 300 and transducer probe 300), a transducer pulse control 310, and at least one processor 320 coupled to the memory 270, communication module 280, display 290, input device(s) 300, and transducer pulse control 310. Communication module 280 enables ultrasound device 230 to communicate with one or more other components of system 200, such as one or more computing devices 210, via a wired or wireless communication network, such as network 220.

As used herein, the term "memory", or any variation thereof, may refer to memories 222, 270. Any such memory may comprise a tangible and non-transitory computer-readable medium (i.e., a medium which does not comprise only a transitory propagating signal per se) comprising or storing computer-executable instructions, such as computer programs, sets of instructions, code, software, and/or data for execution of any method(s), step(s) or process(es) described herein by any processor(s) described herein, including processor(s) 260, 320. As used herein, the terms "processor", "processors" or "processor(s)" may refer to any combination of processor(s) 260, 320 suitable for carrying out method step(s) described herein. Memory may comprise one or more of a local and/or remote hard disk or hard drive, of any type, ROM (read-only memory) and/or RAM (random-access memory), buffer(s), cache(s), flash memory, optical memory (e.g., CD(s) and DVD(s)), and any other form of volatile or non-volatile storage medium in or on which information may be stored for any duration. Such computer-executable instructions, when executed by the processor(s) of computing device(s) 210 and/or ultrasound device(s) 230, cause the processor(s) 260, 320 to perform any of the methods described herein, such as methods for predicting tumor response to neoadjuvant chemotherapy (NAC).

While the foregoing has been described in some detail for purposes of clarity and understanding, it will be appreciated by those skilled in the relevant arts, once they have been made familiar with this disclosure, that various changes in form and detail can be made without departing from the true scope of the appended claims. The present application is therefore not to be limited to the exact components or details of methodology or construction set forth above. Except to the extent necessary or inherent in the processes themselves, no particular order to steps or stages of methods or processes described in this disclosure, including in the Figures, is intended or implied, and the order of process or method steps may be varied and/or made sequential or parallel without changing the purpose, effect, or import of the method(s) described.

REFERENCES

[1] I. A. for R. on C. (Iarc). WHO, "GLOBOCAN 2012: Estimated Cancer Incidence, Mortality and Prevalence Worldwide in 2012.," Globocan, pp. 1-6, 2012.
[2] C. J. L. Murray and A. D. Lopez, "Mortality by cause for eight regions of the world: Global Burden of Disease Study," Lancet, vol. 349, no. 9061, pp. 1269-1276 May 1997.
[3] F. Bray, J. Ferlay, I. Soerjomataram, R. L. Siegel, L. A. Torre, and A. Jemal, "Global cancer statistics 2018: GLOBOCAN estimates of incidence and mortality worldwide for 36 cancers in 185 countries," CA. Cancer J. Clin., vol. 68, no. 6, pp. 394-424, November 2018.
[4] G. N. Hortobagyi, "Comprehensive management of locally advanced breast cancer," Cancer, vol. 66, no. 6 Suppl, pp. 1387-91, September 1990.
[5] S. H. Giordano, "Update on Locally Advanced Breast Cancer," Oncologist, vol. 8, no. 6, pp. 521-530, 2003.
[6] B. Fisher et al., "Effect of preoperative chemotherapy on the outcome of women with operable breast cancer," J. Clin. Oncol., vol. 16, no. 8, pp. 2672-2685, 1998.
[7] S. J. Cleator, a Makris, S. E. Ashley, R. Lal, and T. J. Powles, "Good clinical response of breast cancers to neoadjuvant chemoendocrine therapy is associated with improved overall survival.," Ann. Oncol., vol. 16, no. 2, pp. 267-72, February 2005.
[8] V. Guarneri et al., "Prognostic value of pathologic complete response after primary chemotherapy in relation to hormone receptor status and other factors," J. Clin. Oncol., vol. 24, no. 7, pp. 1037-44, March 2006.
[9] D. Sethi, R. Sen, S. Parshad, S. Khetarpal, M. Garg, and J. Sen, "Histopathologic changes following neoadjuvant chemotherapy in locally advanced breast cancer," Indian J. Cancer, vol. 50, no. 1, pp. 58-64, 2013.
[10] S. Chuthapisith, J. M. Eremin, M. El-Sheemy, and O. Eremin, "Neoadjuvant chemotherapy in women with large and locally advanced breast cancer: Chemoresistance and prediction of response to drug therapy," Surgeon, vol. 4, no. 4. Edinburgh University Press, pp. 211-219, August-2006.
[11] W. Haque, V. Verma, S. Hatch, V. Suzanne Klimberg, E. Brian Butler, and B. S. Teh, "Response rates and pathologic complete response by breast cancer molecular subtype following neoadjuvant chemotherapy," Breast Cancer Res. Treat., vol. 170, no. 3, pp. 559-567, August 2018.
[12] T. Byrski et al., "Pathologic complete response rates in young women with BRCA1-positive breast cancers after neoadjuvant chemotherapy," J. Clin. Oncol., vol. 28, no. 3, pp. 375-379, January 2010.
[13] K. Brindle, "New approaches for imaging tumour responses to treatment," Nat. Rev. Cancer, vol. 8, no. 2, pp. 94-107, February 2008.
[14] B. T. Hennessy et al., "Outcome after pathologic complete eradication of cytologically proven breast cancer axillary node metastases following primary chemotherapy," J. Clin. Oncol., vol. 23, no. 36, pp. 9304-11, December 2005.
[15] J. B. Nikas, W. C. Low, and P. A. Burgio, "Prognosis of treatment response (pathological complete response) in breast cancer," Biomark. Insights, vol. 7, pp. 59-70, January 2012.
[16] O. J. Stoetzer et al., "Prediction of response to neoadjuvant chemotherapy in breast cancer patients by circulating apoptotic biomarkers nucleosomes, DNAse, cytokeratin-18 fragments and survivin," Cancer Lett., vol. 336, no. 1, pp. 140-148, August 2013.
[17] H. Schwarzenbach and K. Pantel, "Circulating DNA as biomarker in breast cancer," Breast Cancer Research, vol. 17, no. 1. BioMed Central Ltd., p. 136, October-2015.
[18] S.-J. Dawson et al., "Analysis of circulating tumor DNA to monitor metastatic breast cancer," N. Engl. J. Med., vol. 368, no. 13, pp. 1199-209, March 2013.
[19] J. Czernin and M. E. Phelps, "Positron emission tomography scanning: current and future applications," Annu. Rev. Med., vol. 53, pp. 89-112, January 2002.
[20] B. S. Pio et al., "Usefulness of 3'-[F-18]fluoro-3'-deoxythymidine with positron emission tomography in predicting breast cancer response to therapy," Mol. imaging Biol., vol. 8, no. 1, pp. 36-42, 2006.
[21] C.-P. Chou et al., "Monitoring breast cancer response to neoadjuvant systemic chemotherapy using parametric contrast-enhanced MRI: a pilot study," Acad. Radiol., vol. 14, no. 5, pp. 561-73, May 2007.
[22] J. Mamou and M. L. Oelze, Eds., Quantitative Ultrasound in Soft Tissues. Dordrecht: Springer Netherlands, 2013.
[23] E. J. Feleppa et al., "Typing of prostate tissue by ultrasonic spectrum analysis," IEEE Trans. Ultrason. Ferroelectr. Freq. Control, vol. 43, no. 4, pp. 609-619, July 1996.
[24] M. Yang, T. M. Krueger, J. G. Miller, and M. R. Holland, "Characterization of anisotropic myocardial backscatter using spectral slope, intercept and midband fit parameters," Ultrason. Imaging, vol. 29, no. 2, pp. 122-34, April 2007.
[25] D. J. Coleman, F. L. Lizzi, R. H. Silverman, L. Helson, J. H. Torpey, and M. J. Rondeau, "A model for acoustic characterization of intraocular tumors.," Invest. Ophthalmol. Vis. Sci., vol. 26, no. 4, pp. 545-50, April 1985.
[26] H. Tadayyon, A. Sadeghi-Naini, L. Wirtzfeld, F. C. Wright, and G. J. Czarnota, "Quantitative ultrasound characterization of locally advanced breast cancer by estimation of its scatterer properties," Med. Phys., vol. 41, no. 1, p. 012903, January 2014.
[27] H. Tadayyon, A. Sadeghi-Naini, and G. J. Czarnota, "Noninvasive characterization of locally advanced breast cancer using textural analysis of quantitative ultrasound parametric images," Transl. Oncol., vol. 7, no. 6, pp. 759-767, December 2014.
[28] A. Sadeghi-Naini et al., "Quantitative ultrasound spectroscopic imaging for characterization of disease extent in prostate cancer patients," Transl. Oncol., vol. 8, no. 1, pp. 25-34, February 2015.
[29] A. Sadeghi-Naini et al., "Low-frequency quantitative ultrasound imaging of cell death in vivo," Med. Phys., vol. 40, no. 8, p. 082901, July 2013.
[30] H. Tadayyon et al., "Quantitative ultrasound assessment of breast tumor response to chemotherapy using a multi-parameter approach," Oncotarget, vol. 7, no. 29, pp. 45094-45111, 2016.

[31] L. Sannachi et al., "Non-invasive evaluation of breast cancer response to chemotherapy using quantitative ultrasonic backscatter parameters," Med. Image Anal., vol. 20, no. 1, pp. 224-236, November 2014.

[32] A. Sadeghi-Naini et al., "Quantitative ultrasound evaluation of tumor cell death response in locally advanced breast cancer patients receiving chemotherapy," Clin. Cancer Res., vol. 19, no. 8, pp. 2163-74, April 2013.

[33] A. Sadeghi-Naini et al., "Conventional frequency ultrasonic biomarkers of cancer treatment response in vivo," Transl. Oncol., vol. 6, no. 3, pp. 234-243, June 2013.

[34] A. Sadeghi-Naini et al., "Chemotherapy-Response Monitoring of Breast Cancer Patients Using Quantitative Ultrasound-Based Intra-Tumour Heterogeneities," Sci. Rep., vol. 7, p. 10352, 2017.

[35] A. Sadeghi-Naini et al., "Early prediction of therapy responses and outcomes in breast cancer patients using quantitative ultrasound spectral texture," Oncotarget, vol. 5, no. 11, pp. 3497-3511, 2014.

[36] L. Sannachi et al., "Response monitoring of breast cancer patients receiving neoadjuvant chemotherapy using quantitative ultrasound, texture, and molecular features," PLOS One, vol. 13, no. 1, p. e0189634, January 2018.

[37] H. Tadayyon et al., "A priori prediction of neoadjuvant chemotherapy response and survival in breast cancer patients using quantitative ultrasound," Sci. Rep., vol. 7, p. 45733, 2017.

[38] J. P. B. O'Connor, C. J. Rose, J. C. Waterton, R. A. D. Carano, G. J. M. Parker, and A. Jackson, "Imaging intratumor heterogeneity: Role in therapy response, resistance, and clinical outcome," Clin. Cancer Res., vol. 21, no. 2, pp. 249-257, 2015.

[39] M. Byra, A. Nowicki, H. Wróblewska-Piotrzkowska, and K. Dobruch-Sobczak, "Classification of breast lesions using segmented quantitative ultrasound maps of homodyned K distribution parameters," Med. Phys., vol. 43, no. 10, pp. 5561-5569, 2016.

[40] L. G. Martelotto, C. K. Y. Ng, S. Piscuoglio, B. Weigelt, and J. S. Reis-Filho, "Breast cancer intra-tumor heterogeneity," Breast Cancer Research, vol. 16, no. 3. BioMed Central Ltd., p. 210, May-2014.

[41] S. P. Evans, Andy, Ian Ellis and A. J. (Andrew J. Evans, Breast calcification: a diagnostic manual. Greenwich Medical Media, 2002.

[42] J. Wu, G. Gong, Y. Cui, and R. Li, "Intratumor partitioning and texture analysis of dynamic contrast-enhanced (DCE)-MRI identifies relevant tumor subregions to predict pathological response of breast cancer to neoadjuvant chemotherapy," J. Magn. Reson. Imaging, vol. 44, no. 5, pp. 1107-1115 November 2016.

[43] Q. Wang, "GMM-Based Hidden Markov Random Field for Color Image and 3D Volume Segmentation," arXiv, pp. 1212.4527 (1-7), 2012.

[44] E. a Eisenhauer et al., "New response evaluation criteria in solid tumours: revised RECIST guideline (version 1.1)," Eur. J. Cancer, vol. 45, no. 2, pp. 228-47, January 2009.

[45] K. N. Ogston et al., "A new histological grading system to assess response of breast cancers to primary chemotherapy: Prognostic significance and survival," Breast, vol. 12, no. 5, pp. 320-327, 2003.

[46] Y. Labyed, T. A. Bigelow, and B. L. McFarlin, "Estimate of the attenuation coefficient using a clinical array transducer for the detection of cervical ripening in human pregnancy," Ultrasonics, vol. 51, no. 1, pp. 34-9, January 2011.

[47] L. X. Yao, J. A. Zagzebski, and E. L. Madsen, "Backscatter coefficient measurements using a reference phantom to extract depth-dependent instrumentation factors," Ultrason. Imaging, vol. 12, no. 1, pp. 58-70, January 1990.

[48] N. Duric et al., "Development of ultrasound tomography for breast imaging: Technical assessment," Med. Phys., vol. 32, no. 5, p. 1375, 2005.

[49] F. L. Lizzi et al., "Comparison of theoretical scattering results and ultrasonic data from clinical liver examinations," Ultrasound Med. Biol., vol. 14, no. 5, pp. 377-385, 1988.

[50] M. F. Insana, R. F. Wagner, D. G. Brown, and T. J. Hall, "Describing small-scale structure in random media using pulse-echo ultrasound," J. Acoust. Soc. Am., vol. 87, no. 1, pp. 179-92, January 1990.

[51] M. L. Oelze, W. D. O'Brien, J. P. Blue, and J. F. Zachary, "Differentiation and characterization of rat mammary fibroadenomas and 4T1 mouse carcinomas using quantitative ultrasound imaging," IEEE Trans. Med. Imaging, vol. 23, no. 6, pp. 764-71, June 2004.

[52] M. F. Insana and T. J. Hall, "Parametric ultrasound imaging from backscatter coefficient measurements: image formation and interpretation.," Ultrason. Imaging, vol. 12, no. 4, pp. 245-67, October 1990.

[53] M. A. Syakur, B. K. Khotimah, E. M. S. Rochman, and B. D. Satoto, "Integration K-Means Clustering Method and Elbow Method for Identification of the Best Customer Profile Cluster," in IOP Conference Series: Materials Science and Engineering, 2018, vol. 336, no. 1.

[54] S. Z. Li, "Markov random field modeling in computer vision," no. January 2011, 2011.

[55] Y. Zhang, M. Brady, and S. Smith, "Segmentation of brain MR images through a hidden Markov random field model and the expectation-maximization algorithm," IEEE Trans. Med. Imaging, vol. 20, no. 1, pp. 45-57, January 2001.

[56] R. F. Wagner, S. W. Smith, J. M. Sandrik, and H. Lopez, "Statistics of Speckle in Ultrasound B-Scans," IEEE Trans. Sonics Ultrason., vol. 30, no. 3, pp. 156-163, 1983.

[57] N. V. Chawla, K. W. Bowyer, L. O. Hall, and W. P. Kegelmeyer, "SMOTE: Synthetic Minority Over-sampling Technique," J. Artif. Intell. Res., vol. 16, pp. 321-357, June 2002.

[58] A. Sadeghi-Naini et al., "Early detection of chemotherapy-refractory patients by monitoring textural alterations in diffuse optical spectroscopic images," Med. Phys., vol. 42, no. 11, pp. 6130-6146 November 2015.

[59] E. Karami et al., "Quantitative MRI Biomarkers of Stereotactic Radiotherapy Outcome in Brain Metastasis.," Sci. Rep., vol. 9, p. 19830, December 2019.

[60] P. M. Lamb, N. M. Perry, S. J. Vinnicombe, and C. A. Wells, "Correlation between ultrasound characteristics, mammographic findings and histological grade in patients with invasive ductal carcinoma of the breast," Clin. Radiol., vol. 55, no. 1, pp. 40-44, 2000.

[61] A. M. Fowler, D. A. Mankoff, and B. N. Joe, "Imaging Neoadjuvant Therapy Response in Breast Cancer," Radiology, vol. 285, no. 2, pp. 358-375, November 2017.

What is claimed is:

1. A computer-implemented method for predicting tumor response to neoadjuvant chemotherapy (NAC), the method comprising:

acquiring, using an ultrasound device, ultrasound radiofrequency (RF) data comprising RF frames and B-mode images from a tumor subject prior to the NAC;

generating, if not acquired at said acquiring step, said B-mode images using the acquired RF data;

identifying a region of interest (ROI) in each of said B-mode images, the ROI comprising a tumor;

generating at least one quantitative ultrasound (QUS) parametric map by QUS spectral analysis or analysis of RF signal envelope statistics of each RF frame associated with said B-mode images throughout the ROI to derive a corresponding QUS parameter, each said QUS parametric map based on a respective said QUS parameter;

identifying distinct intra-tumor regions on the at least one QUS parametric map by applying a classification (clustering) algorithm to the at least one QUS parametric map, wherein the distinct intra-tumor regions are identified as segmented regions;

extracting features from the segmented regions on each of the at least one QUS parametric map within the ROI to characterize the tumor;

determining an optimal QUS biomarker for response prediction;

training a classification algorithm for the response prediction using the optimal QUS biomarker; and classifying the tumor subject into a responder or a non-responder to the NAC using the optimal QUS biomarker in conjunction with the trained classification algorithm, the trained classification algorithm comprising a response prediction model;

wherein:

(i) said determining the optimal QUS biomarker for the response prediction comprises analyzing the features using a multi-step feature selection process to eliminate features that do not contribute to the response prediction, to obtain an optimal QUS feature set for the response prediction, the optimal QUS biomarker comprising the optimal QUS feature set; and (ii) the multi-step feature selection process comprises:

ranking and reducing the features to a reduced feature set using a minimal-redundancy-maximal-relevance (mRMR) method; and selecting the optimal QUS feature set for the response prediction from the reduced feature set using a feature selection method comprising sequential forward selection (SFS), sequential backward selection, or least absolute shrinkage and selection operator (LASSO).

2. The computer-implemented method of claim 1, wherein the tumor is associated with a cancer comprising breast, prostate, liver, or thyroid cancer.

3. The computer-implemented method of claim 1, wherein the tumor comprises a locally advanced breast cancer.

4. The computer-implemented method of claim 1, wherein the generating the at least one QUS parametric map for each of the RF frames associated with said B-mode images comprises generating at least one QUS parametric map for each image plane of each of the B-mode images.

5. The computer-implemented method of claim 1, wherein the at least one QUS parameter comprises a mid-band fit (MBF), a spectral slope (SS), a spectral 0-MHz intercept (SI), an effective scatterer diameter (ESD), an effective acoustic concentration (EAC), or a homodyned K and Nakagami distribution parameter.

6. The computer-implemented method of claim 5, wherein the ROI comprises a tumor core and a tumor margin.

7. The computer-implemented method of claim 6, wherein the tumor margin comprises a thickness of 5 mm around the tumor core.

8. The computer-implemented method of claim 6, wherein the extracting the features from the segmented regions on each of the at least one QUS parametric map within the ROI to characterize the tumor comprises said extracting of the features to characterize the segmented regions and the tumor margin.

9. The computer-implemented method of claim 6, wherein said extracting the features from the segmented regions within the ROI comprises extracting said features from the segmented regions and the tumor margin in the at least one QUS parametric map of said ESD, EAC, MBF, SI, SS, or homodyned K and Nakagami distribution parameters.

10. The computer-implemented method of claim 6, wherein the features comprise mean-value and signal to noise ratio (SNR) of each of the at least one QUS parametric map within the tumor core, mean-value and SNR of each of the QUS parametric maps within the tumor margin, mean-value and SNR of each of the at least one QUS parametric map within each of the segmented regions, a difference between the mean-value of each of two of the segmented regions in each of the at least one QUS parametric map, a proportion area of each of the segmented regions within the tumor core, and a relative area of the tumor margin to the core.

11. The computer-implemented method of claim 1, wherein the features are extracted for all image planes and subsequently averaged over an entire volume of the tumor.

12. The computer-implemented method of claim 1, wherein the features comprise 56 features and the reduced feature set comprises 21 features.

13. The computer-implemented method of claim 12, wherein the optimal QUS feature set comprises four features comprising mean-value of the MBF parametric map within a first of the segmented regions $$(M_1^{MBF}),$$

SNR of the ESD parametric map within the tumor margin $$(SNR_m^{ESD}),$$

SNR of the SI parametric map within the first of the segmented regions $$(SNR_1^{SI}),$$

and the difference between mean-values of the EAC parametric map within the first of the segmented regions and a third of the segmented regions $$(M_{3-1}^{EAC}).$$

14. The computer-implemented method of any one of claim 1, wherein said generating the at least one QUS parametric map comprises computing a normalized power spectrum of the ultrasound RF data acquired from the ROI and deriving the at least one QUS parameter by the QUS spectral analysis of the normalized power spectrum of the ultrasound RF data or by the analysis of the RF signal envelope statistics.

15. The computer-implemented method of claim 1, wherein the distinct intra-tumor regions are identified at pixel level on the at least one QUS parametric map.

16. The computer-implemented method of claim 1, wherein the identifying the distinct intra-tumor regions on the at least one QUS parametric map comprises determining an optimum number of the distinct intra-tumor regions.

17. The computer-implemented method of claim 16, wherein said optimum number of the distinct intra-tumor regions is determined by:

performing intra-tumor segmentation for different numbers of regions;

estimating a clustering quality metric comprising Bayesian information criterion (BIC), Calinski-Harabasz index, or Davies-Bouldin index; and identifying a least number of regions at which the clustering quality metric indicates a diminishing improvement as the optimum number of the distinct intra-tumor regions on the at least one QUS parametric map.

18. The computer-implemented method of claim 17, wherein the clustering quality metric comprising said BIC and the diminishing improvement is indicated by low BIC determined using an elbow method.

19. The computer-implemented method of claim 16, wherein the optimum number of the distinct intra-tumor regions on the at least one QUS parametric map is three.

20. The computer-implemented method of claim 1, wherein the classification (clustering) algorithm is a supervised, unsupervised, or reinforcement machine learning algorithm.

21. The computer-implemented method of claim 1, wherein the responder and the non-responder classification are determined by clinical and/or pathological ground truth classification criteria.

22. The computer-implemented method of claim 21, wherein the clinical and/or pathological ground truth classification criteria comprise:

pathological complete response (pCR) versus non-pCR; or a modified response (MR) grading system based on response evaluation criteria in solid tumors (RECIST) and histopathological criteria, a MR indicating less than 30% reduction in tumor size comprising said non-responder, and a MR indicating 30% or greater reduction in tumor size or low residual tumor cellularity comprising said responder.

23. The computer-implemented method of claim 1, wherein the classification (clustering) algorithm comprises a K-means, a Gaussian mixture model (GMM), a hidden Markov random field (HMRF) expectation maximization (EM) algorithm, or a clustering algorithm with spatial constraints followed by a consensus clustering algorithm.

24. The computer-implemented method of claim 1, wherein the classification (clustering) algorithm comprises a decision tree with adaptive boosting, a random forest, a support vector machine (SVM), an artificial neural network, or a K nearest neighbours (K-NN) algorithm.

25. The computer-implemented method of claim 24, wherein the classification (clustering) algorithm comprises said decision tree with adaptive boosting.

* * * * *